United States Patent [19]

Davies et al.

[11] Patent Number: 5,405,781
[45] Date of Patent: Apr. 11, 1995

[54] ION MOBILITY SPECTROMETER APPARATUS AND METHOD, INCORPORATING AIR DRYING

[75] Inventors: John H. Davies, Port Credit; Frank J. Kuja, Brampton; Sydney T. Wiles, all of Mississauga, Canada

[73] Assignee: Barringer Research Limited, Rexdale, Canada

[21] Appl. No.: 124,064

[22] Filed: Sep. 21, 1993

[51] Int. Cl.$^6$ ............................................. G01N 35/08
[52] U.S. Cl. ..................... 436/52; 436/175; 436/807; 422/89; 422/98; 72/23.36; 72/863.12
[58] Field of Search ................. 436/174, 175, 52, 807; 73/863.11, 863.12, 863.21, 863.23, 23.36, 23.2, 23.4–23.42; 422/98, 99, 83

[56] References Cited

U.S. PATENT DOCUMENTS

| | | | |
|---|---|---|---|
| H431 | 2/1988 | Miller | 250/336.1 |
| 3,621,239 | 11/1971 | Cohen | 250/41.9 TF |
| 3,626,179 | 12/1971 | Cohen | 250/41.9 TF |
| 3,626,180 | 12/1971 | Carroll et al. | 250/41.9 TF |
| 3,697,748 | 10/1972 | Cohen | 250/41.9 TF |
| 3,788,479 | 1/1974 | Szakasits | 210/198 C |
| 4,056,969 | 11/1977 | Barringer | 250/255 |
| 4,259,573 | 3/1981 | Prober et al. | 250/287 |
| 4,311,669 | 1/1982 | Spangler | 422/98 |
| 4,551,624 | 11/1985 | Spangler | 250/287 |
| 4,580,440 | 5/1986 | Reid | 73/23 |
| 4,718,268 | 1/1988 | Reid | 73/23 |
| 4,745,227 | 5/1988 | Banar et al. | 250/288 |
| 4,775,795 | 10/1988 | Biehl et al. | 250/379 |
| 4,777,363 | 10/1988 | Eiceman et al. | 250/286 |
| 4,783,201 | 11/1988 | Rice et al. | 55/16 |
| 4,987,767 | 1/1991 | Corrigan | 73/23.36 |
| 4,988,628 | 1/1991 | Nanji | 436/173 |
| 5,037,611 | 8/1991 | Ledford, Jr. | 436/171 |
| 5,071,777 | 12/1991 | Barbour et al. | 436/153 |
| 5,242,836 | 9/1993 | Ruse | 436/178 |

OTHER PUBLICATIONS

Eiceman, "Advances in Ion Mobility Spectrometry: 1980–1990" vol. 22 #1.2 *Critical Reviews in Analytical Chemistry*, 1991.
Forensic Science International (1987), 34, 73, A. H. Lawrence, Detection of Drug Residues on the Hands of Subjects by Surface Sampling and Ion Mobility Spectrometry.
266B Analytical Chemistry (1988), 60, 104, A. H. Lawrence et al., Detection of Ethylene Glycol Dinitrate Vapours by Ion Mobility Spectrometry Using Chrolide Reagent Ions.
Analytical Chemistry (1986), 58, 361, S. Rokushika et a., Ion Mobility Spectrometry in Carbon Dioxide.
Analytical Chemistry, (1988), 60, 2240, R. L. Eatherton et al., Comparison of Ion Mobility Constants of Selected Drugs After Capillary Gas Chromatography and Capillary Supercritical Fluid Chromatography.
Journal of Chromatography (1976), 117, 327, S. W. Karasek et al., Plasma Chromatography of Heroin and Cocaine with Mass Identified Mobility Spectra.
Analytical Chemistry (1986), 58, 1269, A. H. Lawrence, Ion Mobility Spectrometry/Mass Spectrometry of Some Prescription and Illicit Drugs.

*Primary Examiner*—James C. Housel
*Assistant Examiner*—Rachel Heather Freed
*Attorney, Agent, or Firm*—Bereskin & Parr

[57] ABSTRACT

An ion mobility spectrometer for detecting substances such as narcotics and explosives, has inlets for a sample gas and a drift gas. The gas can be ambient air, bottled air, or another gas source. To ensure accuracy and prevent drifting of analyte peaks, the air is dried. A two stage dryer is provided comprising a first dryer, preferably a dryer which chills the air and removes water by condensation. This removes the bulk of the water. The second dryer includes a suitable absorbent, and reduces the water content to around 1–10 μg/L, i.e. a level which will not substantially affect the performance of the IMS apparatus. The first dryer substantially reduces the load on the second dryer, and enables an extended period of use before the absorbent material in the second dryer either needs to be replaced or regenerated. The increased stability of calibrant and analyte peak positions allows detection windows to be narrowed, resulting in significantly lower false alarm rates.

16 Claims, 6 Drawing Sheets

ION MOBILITY SPECTROMETER APPARATUS AND METHOD, INCORPORATING AIR DRYING

FIELD OF THE INVENTION

This invention relates to chemical detection based on the collection and analysis of surface residues and particles. It particularly relates to analysis in an ion mobility spectrometer (IMS) indicating drying of air. It more particularly relates to the detection with low false alarms of explosives and various contraband items, such as drugs and narcotics in baggage and cargo and on passengers using various modes of transportation, using the technique of ion mobility spectroscopy (IMS).

BACKGROUND OF THE INVENTION

There is currently an increasing problem in many countries with the smuggling of illicit or illegal substances, such as drugs and narcotics, and also various substances which are legal but subject to high tariffs making smuggling attractive; generally the illicit or illegal substances are the major concern. A further problem is the transportation of explosives, either illegally in the nature of smuggling, or with the intention of being used as part of a terrorist threat or attack on a ship, aircraft or the like.

Consequently, there is increasing demand for detection equipment for use at airports, seaports, border crossings, etc. to enable authorities of individual countries to detect such substances, whether carried by individuals, in baggage carried by an individual, or in large, commercial transportation containers and the like.

Such detection equipment is used increasingly in the screening of baggage for explosives, and commonly relies on the collection of vapors which are subsequently analyzed by mass spectrometric or chromatographic techniques. Detection of modern plastic explosives and illicit drugs, such as heroin and cocaine, by such vapor collection is difficult, and frequently impossible, because of factors such as: the extremely low vapor pressures of explosives and narcotics; the small amounts of vapors emanating from these explosives and drugs requiring high volume sampling and very high sensitivity of detection; these explosives and drugs being easily concealed in a variety of baggage or personal articles inhibiting the collection of vapors; the frequent presence of toilet articles, perfumes, cosmetics and the like on persons, belongings, and baggage, producing vapors containing molecules with some properties similar to the targets of interest, thus further complicating the analysis.

Handling of explosives and/or drugs etc. and attempts at their concealment results in minute surface contamination from trace residues of these substances. Similarly, the packaging of drugs, such as cocaine and heroin, for concealment in baggage or cargo is equally difficult to achieve without similar surface contamination. With exceptional measures being taken, such traces will be present, and are in sufficient quantity, although minute, to enable them to be collected through a variety of means, and to be subsequently analyzed by IMS.

Inherent in the detection of small quantities is the possibility of unacceptable False Alarm Rates (FAR).

In general, the smaller the quantity that can be detected, i.e. the more sensitive the detection equipment, the greater the possibility of a False Alarm. This can be caused by detection of spurious trace quantities present from another source, e.g. because the user has just handled a contaminated article; residue from a previous test that was lodged in the apparatus, but becomes dislodged and drawn through the apparatus.

Thus, IMS affords a well-established technique for the detection of drugs and explosives, but because of its high sensitivity interferences can occur and cause false alarms. If FAR are excessive, the instrument can have little practical value to security screeners and customs officers, and users will have little confidence in the instrument. It would enhance the value of the equipment if the FAR is reduced to the minimum possible.

A major cause of interference and instability in IMS is the presence of water vapor and other contaminants in drift gas. For obvious operational convenience, air is generally used as the drift gas in customs and security screening locations. Ambient air has to be dried to a high degree before use, to avoid these problems. Additionally, chemical scrubbing with charcoal or the like is used to remove other contaminants from the air, such as trace hydrocarbons often present in urban atmospheres from automotive traffic, airport traffic, or industrial operations. In laboratory situations IMS instrumentation can be run from compressed, dried air, called zero air, but this is impractical and too costly for actual use.

Another source of interference is the presence of cosmetics, toilet articles and other articles on travellers and in their belongings. These may cause spurious alarms due to chemical signature interferences in IMS, unless the IMS incorporates superior peak discrimination capabilities. Some legal substances can give chemical signatures that are difficult to differentiate from illegal substances of interest.

SUMMARY OF THE INVENTION

In accordance with a first aspect of the present invention there is provided a method of detecting the presence of an analyte in an ion mobility spectrometer apparatus having a drift region, a first inlet for drift gas at one end of the drift region, an outlet for exhaust gas connected to the drift region, a second inlet, and means for applying an electric field across the drift region including a collector electrode, the method comprising:

(a) drying a supply gas to remove a major portion of the water vapor in a first drying device capable of generally continuous operation;

(b) subjecting the supply gas to secondary drying in a second drying device capable of only a finite period of operation, to reduce water vapor content to a concentration level sufficient to prevent any substantial effect on at least one predetermined analyte peak position wherein removal of a major portion of the water vapor in step (a) extends the effective operating period of the second drying device;

(c) passing the supply gas through the drift region, as a drift gas;

(d) introducing vapor of at least one analyte through the second inlet into the drift region; and (e) detecting the presence of each analyte from the drift time through the drift region.

Preferably, the IMS device includes an ionization region, and a gating grid separating the ionization region from the drift region. The second inlet then opens into the ionization region and the outlet is connected to the ionization region, preferably adjacent the gating grid. The dried supply gas is then also supplied to the second inlet as a carrier gas for entraining the analyte vapor.

Preferably, the gas is first dried by chilling to a low temperature to remove water vapor by condensation. This technique can be carried out continuously, without any degradation in its performance. The gas can be chilled to 2° to 6° C., by a thermo-electric cooler.

The second drying step is preferably carried out by an absorbent, capable of reducing the water content to about 1 to 10 $\mu$g/L or minus 60° C. to minus 100° C. dew point. The absorbent could be calcium sulphate, phosphorus pentoxide, or molecular sieve, or proprietary material based on these substances, and containing appropriate color indicators, to indicate the moisture content of the absorbent material.

The present invention also provides a corresponding ion mobility spectrometer apparatus, the apparatus comprising:

an ion mobility spectrometer having a drift region, a first inlet for a drift gas at one end of the drift region, an outlet for exhaust gas connected to the drift region, means for applying an electric field across the drift region including a collector electrode, means for introducing a sample vapor into the drift region, and means for analysing an output of the collector electrode;

a first dryer having a main gas inlet for a supply gas, for removing the bulk of the water vapor in the gas; and a second dryer having an inlet connected to the first dryer and outlet connected to the first inlet.

Again, the spectrometer preferably includes an ionization region. The first dryer preferably chills the gas to remove water vapor by condensation, while the second dryer includes an absorbent material for absorbing water vapor.

The two-stage dryer efficiently removes water vapor from the drift gas over an extended period of time, thereby producing IMS ion peaks that remain very stable in position over long periods of time, and thereby allowing the use of very narrow IMS time intervals in which to locate the ion peak of the species of interest, to more effectively discriminate that peak from close by ion peaks of chemical interferences.

The invention can be used in the IMS analysis of minute particulate contamination collected from the surfaces of objects being inspected by security personnel in situations where real-time detection with low FAR is essential. The better discrimination provided by the invention provides lower FARs than hitherto possible. The better ion stability provided by the invention allows many weeks of instrument operation without recalibration.

The present invention utilises the improved ion and IMS peak position stabilities to effectively and efficiently select, discriminate, and confirm the presence of IMS peaks for the ionic species of interest, through the use of algorithms and associated electronics, and optionally through the use of the IMS peak position of a calibrant ion. This aspect of the invention results in faster data processing, thereby allowing more data to be used and more peaks to be monitored simultaneously, all within the time frame required for real-time detection of surface contamination. This increased data processing capability results in greater accuracy, lower FARs, and the capability of monitoring for more species of interest.

In contrast, most conventional IMS instruments using air as drift gas experience a rapid deterioration in air-drying efficiency, causing the position of IMS peaks to change significantly with time, thereby requiring the use of wider detection intervals, resulting in increased interference from other peaks appearing within these intervals, thereby producing higher FARs.

BRIEF DESCRIPTION OF THE DRAWING FIGURES

For a better understanding of the present invention, and to show more clearly how it may be reduced to practice, reference will now be made, by way of example, to the accompanying drawings which show a preferred embodiment of the present invention and in which.

DESCRIPTION OF PREFERRED EMBODIMENT

Figure 1:
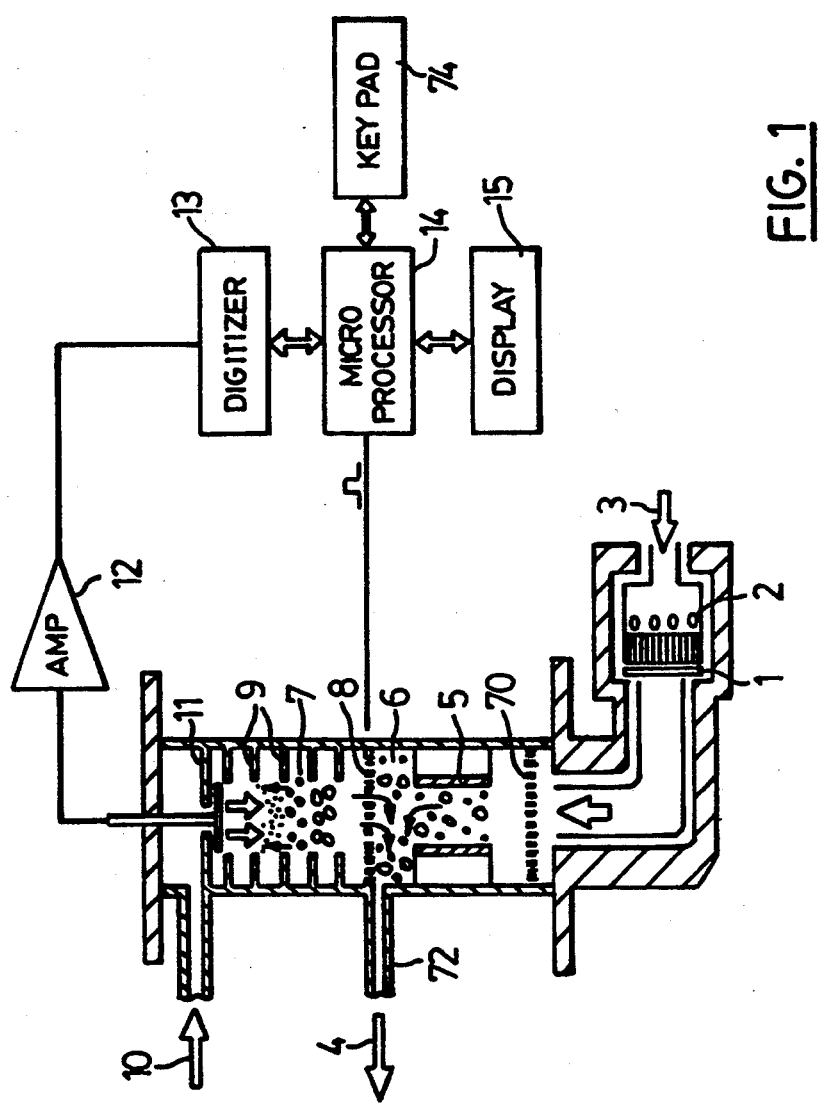
FIG. 1 is a schematic of an IMS detection apparatus in accordance with the present invention.

An apparatus in accordance with the present invention includes an IMS detector 4, which is depicted in FIG. 1, and which makes use of ion mobility principles to respond selectively to substances of interest.

The apparatus has an inlet 3 for the sample carrier gas, in this case air, including a reactant if required. A sample substrate 1 is placed adjacent a desorber heater 2, and the sample carrier gas is processed through the desorber heater 2 and sample 1.

A conduit guides the gas flow to a reaction region 6 of the IMS device. This includes a repelling ring 70 at the inlet for gas, and an ionizing source 5. An outlet for an exhaust gas flow is indicated at 72.

A gating grid 8 separates the ionization or reaction region 6 from a drift region 7. The drift region 7 has a series of focusing rings 9 around it, and a collector electrode 11 at its end remote from the repelling ring 70.

An inlet 10 is provided for a drift gas flow, including a calibrant.

The collector electrode 11 is connected through an amplifier 12 to a digitizer 13. This in turn is connected to a microprocessor 14, connected to a display 15 and key pad 74, in a known manner.

The detailed electronics of the IMS device do not form part of the present invention, and can be conventional. It is sufficient to note that an electric field is applied between the collector electrode 11 and repelling ring 70, to cause certain species of ions to tend to drift towards the collector electrode 11. Passage of ions from the ionization or reaction region 6 is controlled by the gating grid 8, as detailed below.

In use, a sample of microscopic dust is collected from the surface under investigation through the process of either swabbing, wiping, or vacuum suction and/or abrasion via a sampling head, with the sample being collected on an inert substrate indicated at 1. The substrate 1 is placed in the IMS device 4, as shown. Vapors are liberated from the substrate 1 by application of the desorber heater 2, and are subsequently carried into the reaction region 6 by the carrier gas flow 3. In the reaction or ionization region 6, the carrier gas and trace vapors are ionized by the weak radioactive source 5. As a result of complex interchange reactions which take place in the reaction region 6, the molecules of certain species in the vapor form ions and ionic clusters, both of which are hereafter designated as ions, while others do not. The ions are prevented from entering the drift region 7 by the potential of the charged gating grid 8. When the gating charge is changed to a lower potential, the ions can enter the drift region 7; with the higher gating charge or potential present, the ions are prevented from entering the drift region 7 and exit through exhaust 72. After entering the drift region 7, the ions are accelerated, under the influence of a strong electric field applied through focusing rings 9, through the drift region 7 against a flow of drift gas 10 towards the collector electrode 11. Their arrival time at the collector electrode 11, the "drift time", is a function of each ion's characteristic mobility and is a characteristic of the individual species. These species are therefore classified according to their ability to be ionized, and to the relative mobilities of the ions produced.

The weak ionic current through the collector electrode 11 is amplified in the amplifier 12, digitized at 13 and processed by the microprocessor 14, employing algorithms for discrimination of the desired species from any interfering vapor present in the sample as background. The resulting identification of the drug or explosive compound is reported on a liquid crystal display 15 and also as a visual and audio alarm.

Ambient air is used to provide supply gas for use as the drift and sample carrier gases for IMS operation. Other gas sources, e.g. bottled air or another gas, can be used. Acceptable operation of an IMS is obtained when the water content of air is very low, about 1–10 μg/L (−60° C. to −100° C. dew point). Although this water content level is achievable by means of a drying tube containing a proprietary dryer based on calcium sulphate or similar material, it is well recognized that the water-removing efficiency of such tubes becomes increasingly less efficient as the material within the tube is gradually deactivated, leading to an increasing water content in the drift gas. Water molecules cluster with sample and calibrant ions in the IMS drift region. The extent of clustering increases with water content, and causes the drift times of the sample and calibrant peaks to change to varying extents. Gradually increasing water content in the drift gas therefore results in an ongoing instability in drift times, and to a considerable degree of uncertainty in the sought analyte peak positions.

Figure 2:
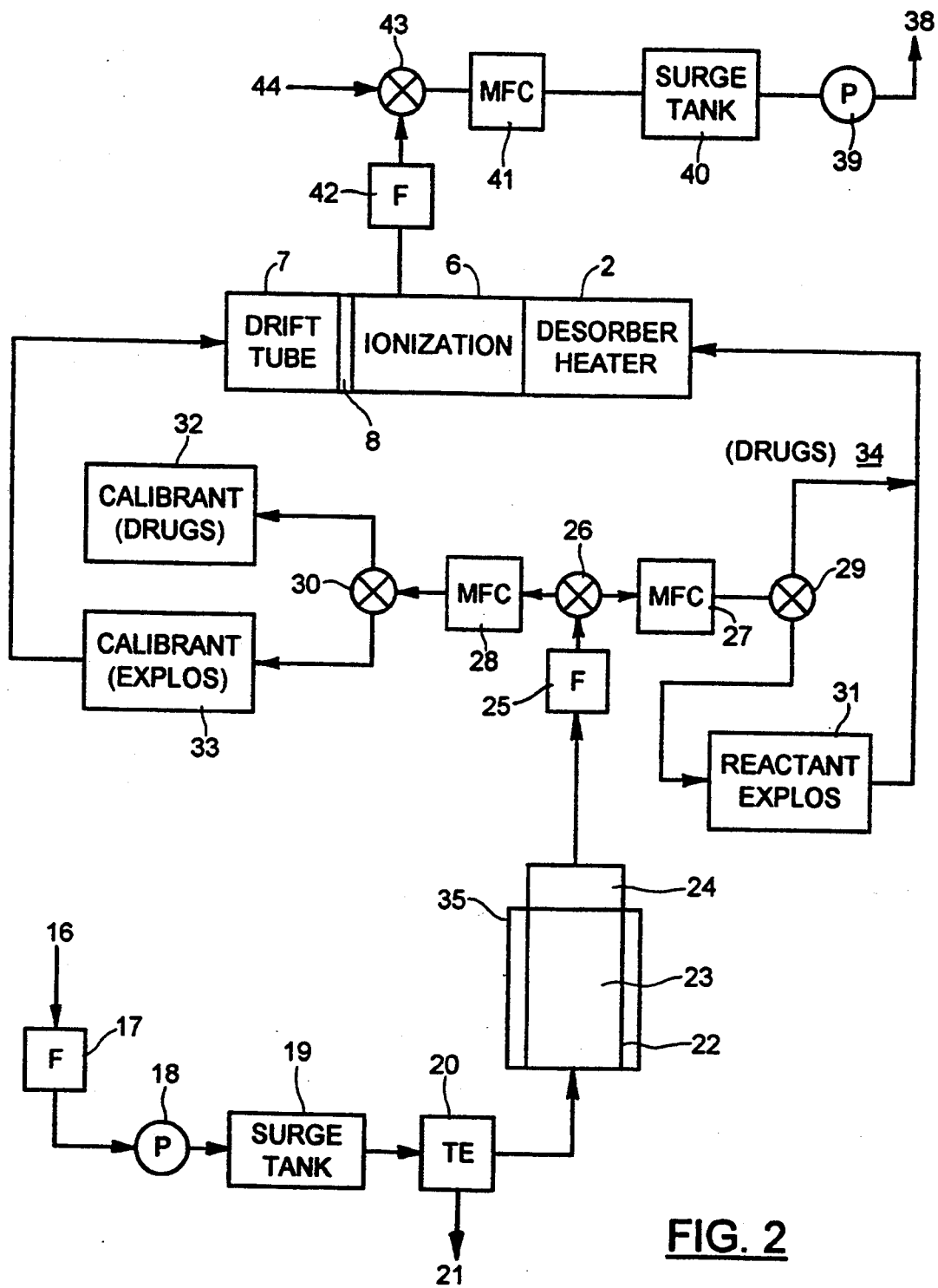
FIG. 2 is a schematic of the air flow circuit.

Referring to FIG. 2, efficient drying of the ambient air, the supply gas, used as drift and carrier gases is achieved over an extended period by means of a two-stage drying process. The ambient air 16 is pumped through a prefilter 17, to remove large particulate contamination, by a membrane pump 18 with the flow being stabilized by a surge tank 19. The first stage of drying is by means of a thermo-electric (TE) cooler 20 which chills the moist incoming air to 2° to 6° C. and thus removes a major portion of the water by condensation which is removed at 21. The predried air then proceeds to the second stage in a large capacity drying tube 22 containing calcium sulphate 23 or other drying agents such as phosphorous pentoxide or molecular sieves, where the water content is reduced to the 1–10 μg/L level. A small portion at the end of the drying tube 22 contains activated charcoal 24 to remove organic contaminants from the air. The dry air then passes through another filter 25, to remove any extraneous contamination, before being split at 26 into drift gas and sample carrier gas flows.

The flows of carrier gas and drift gas are controlled by respective mass flow controllers 27, 28, after which each proceeds by alternate routes, selected by three way switches 29, 30, dependent on whether drugs or explosives are being analyzed. A reactant 31 is added to the sample carrier gas to assist in ionization reaction chemistry when explosives are being analyzed; such a reactant is not needed for drug analysis and the carrier gas flows through line 34. Appropriate calibrants are added to the drift gas for the analysis of drugs 32 and explosives 33 by means of a permeation tube bleed. The drift and carrier gases then proceed to opposite ends of the IMS detector. The drift gas passes through the drift tube 7 and the gating grid 8 before exiting through the exhaust 52 at the grid end of the ionization chamber 6. The carrier gas carries the desorbed sample vapors into the ionization chamber 6 before going to the common exhaust 52. Typical gas flows are 250 to 350 cc/min for drift gas and 150 to 350 cc/min for carrier gas. The drift gas always flows through the IMS detector when the unit is in operation, even when not in the sample analysis mode. This constant flow purges the unit between sample analysis, thus eliminating memory effects, and provides a means of constantly monitoring the calibrant ion peak stability.

The exhaust gas is drawn from the IMS by a second membrane pump 39 with the flow controlled by a surge tank 40 and a mass flow controller 41. The exhaust gas flow, typically 500 cc/min, is the sum of the drift and carrier gas flows. The exhaust is cleaned up by a filter 42, typically packed glass wool, to remove pollutants. A three way switch 43 allows purge air 44 to be introduced into the exhaust gas line when the IMS is not in the sample analysis mode.

Removal of water by the first-stage TE chiller 20 significantly reduces the load on the second-stage drier material, thereby significantly increasing its life as an efficient provider of dry air at the required level of water content. Furthermore, the second-stage drier material can be reactivated by in situ heating, shown at 35. In known manner, the absorbent or drying agent in the tube 22 can include a color indicator, to indicate the state of the absorbent, which in turn enables the activation to be carried out at appropriate times. This two-stage drying results in an up to 10-fold increase in effective life of drying material compared to a tube of similar dimensions without an upstream chiller. The two-stage drying process results in several weeks of IMS operation with a drift gas of essentially constant, low water content, before the drying material requires replacement. As detailed below, the increased stability permits halving of the width of the IMS detection time windows, and results in a five- to ten-fold improvement in the FAR.

Figure 3:
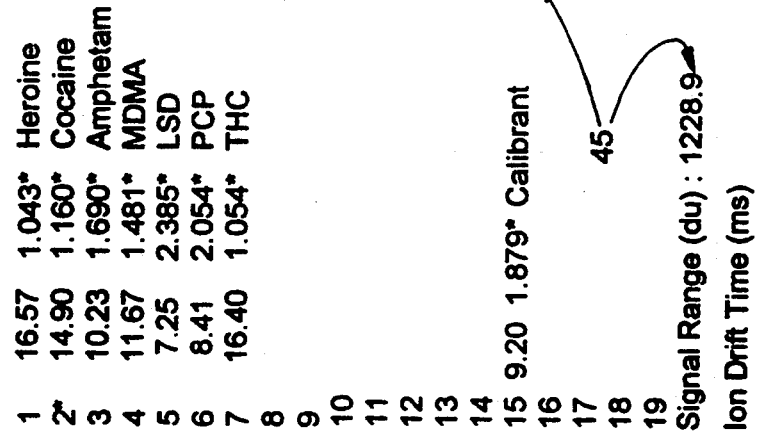
FIG. 3 depicts a typical plasmagram obtained from an IMS apparatus of FIG. 1.

FIG. 3 depicts a typical plasmagram generated by an IMS as configured in FIG. 1. The vertical axis 45 is the amplitude of the detected ion current, and is proportional to the amount of material desorbed, ionized and collected. The vertical axis can be scaled in mA of ion current or more usually digital units of signal detected. The horizontal axis 46, in milliseconds, represents the drift times for the various ion analytes. It should be remembered that a drift time for a sought analyte depends not only on analyte ion factors such as molecular weight and shape but also upon various instrument parameters such as accelerating voltage across the drift tube, length of the drift tube, pressure within the drift tube, temperature, amongst others. FIG. 3 shows the results obtained from 1 μl of a 600 pg/μl solution of cocaine in methanol, as indicated at the top of the Figure. The plasmagram presentation identifies the time location of sought analytes listed at the left of FIG. 3. For example peak 15 is the calibrant, and peak 2 is the sought cocaine peak. The plasmagram additionally shows the settings of various instrument parameters such as timing, signal averaging arrangements, temperature settings (desorbing, inlet and drift tube), gas flows, and accelerating voltage 47.

In FIG. 3, the window or time during which the sample is taken is indicated as "Wind" in the top right-hand corner. The drift time is given in millisec. and the reduced mobility is indicated as Red Mobil, in units of $cm^2$/volt.sec.

Along the bottom, the Signal Range gives the vertical scale.

The total number of windows making up the complete window is indicated as "Wnds". Each of these windows comprises a certain number of sweeps indicated as "Swps" and each spaced at an interval δT. Each sweep in turn comprises a number of points indicated as "Pts", spaced by time interval indicated at δT. Thus, in this case, the spacing of the points was 25 μs. and there are 776 points in each sweep, for a total time of 20 ms. With 16 sweeps in each window and a δt of 20 ms, this gives an individual window length of 0.32 seconds. With 14 windows, this gives a total window of 4.48 seconds.

Figure 4A:
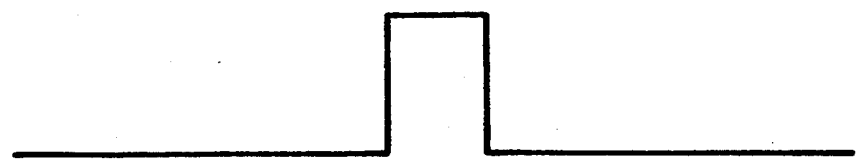
FIGS. 4a and 4b, depict the use of an IMS time window to locate and discriminate a sought peak.
Figure 4B:
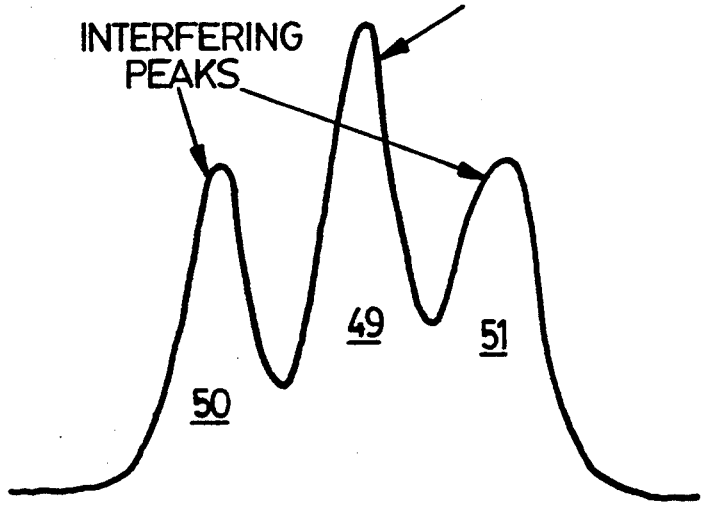

FIG. 4 depicts the method of selecting and discriminating sought analyte ion peaks. The detection window 48, the preset drift time interval in which the IMS detection system looks for the sought ion peak, is shown set over an analyte peak 49 which is the sought target. Two neighboring peaks, 50 and 51, also appear as may be experienced when chemical interferences are present from perfumes, toilet articles, or the like. The detection requirement is to select the analyte peak 49 and reject the interfering peaks 50, 51. Evidently, the narrower the detection window that can be set over the analyte peak 49, the better is the discrimination achieved in that peak, by the rejection of nearby interfering peaks 50, 51.

In an IMS employing single-stage drying, the detection windows are typically 200 to 250 μs to ensure adequate capture of the analyte peak within a 10–20 ms mobility range, i.e. the window is approximately 1% of the mobility. Under the condition of two-stage drying, when very stable peaks are achieved, the detection windows can be reduced typically to 80 to 120 μs i.e. to approximately 0.5% of the mobility. Experiments show that halving of the detection windows reduces the FAR for explosives detection by a factor of 5- to 10-fold, this being a significant improvement over operations in a more conventional IMS with the wider detection windows.

Various methods can be used in IMS instruments to achieve peak detection. They vary dependent upon the use of calibrants, detector electronics, and algorithms. By way of example, consider a three class or step peak detection system, comprising:

a) After start-up, the detection algorithm first searches for the calibrant ion within a relatively wide preset window; the peak is "found" when positions in successive data cycles are within a preset "discriminant" value.

b) Once found, the calibrant ion peak position is monitored, within a narrower window, and updated, by running average, throughout the entire operation, the calibrant monitoring being carried out before and between individual analyses.

c) Target analyte ion peaks are detected at a defined drift time within a narrow window (peak position ±a preset variability); the analyte peak position occurs at a ratio to that of the calibrant ion, based on the ratio of their characteristic reduced ion mobilities, and this is used to set the narrow window for the analyte peak.

If the windows are made too wide, to compensate for ion peak instability, data processing times are longer, incorrect peaks may be selected, and false positive results may be generated. If windows are made reasonably narrow, the detection algorithm may never find the calibrant peak, and may miss target analyte ion peaks, both due to ion peak instability, and this can generate false negative results. Ensuring drift air of low and essentially constant water content over an extended period by means of two-stage drying results in ion peak stability, thereby allowing narrow windows to be used for better selection and discrimination of peaks without incurring the risks described above. The significance of providing stable ion peaks by control of the air drying process can thus be more fully appreciated. Furthermore to one skilled in the art it will be appreciated that whatever detection scheme is applied, accurate detection is dependent on stable analyte peaks; if the detection system has to compensate for excessive peak instability, then accuracy deteriorates.

Figure 5:
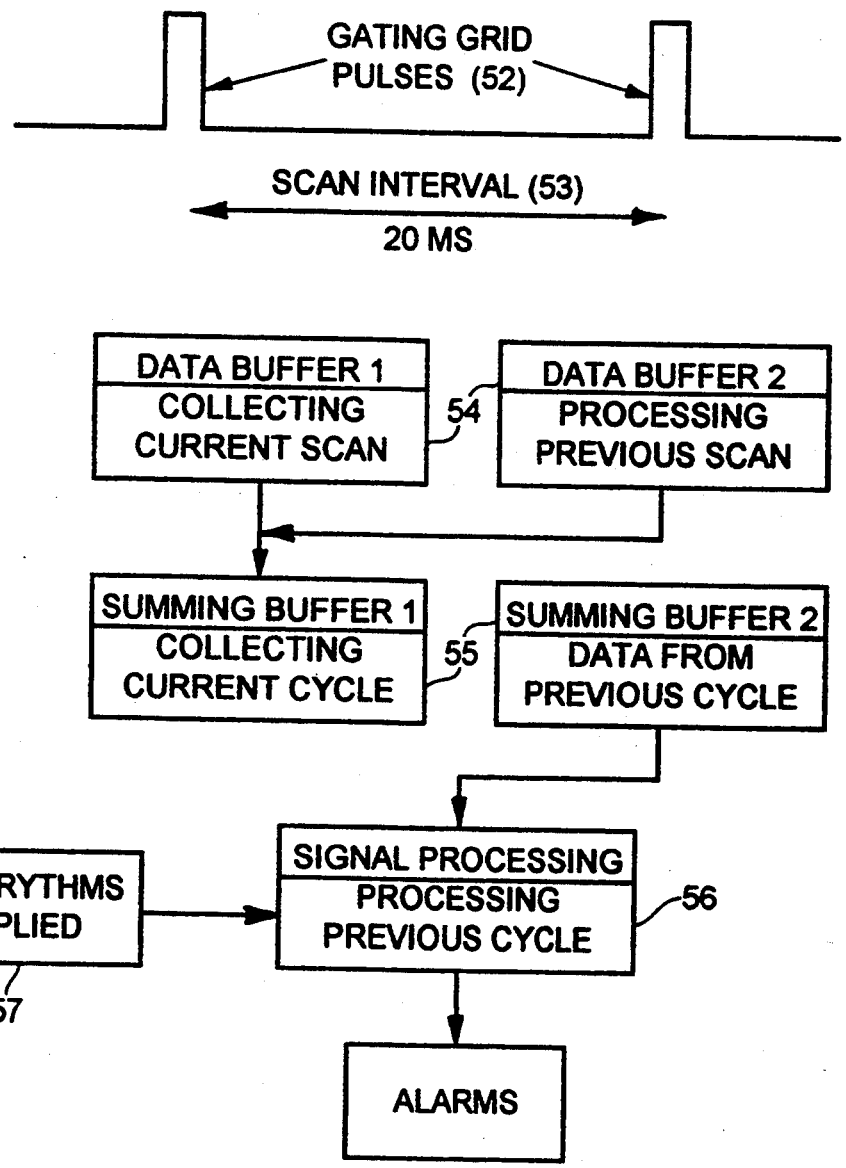
FIG. 5 depicts the detection process electronics schematically.

FIG. 5 shows schematically collection of data and implementation of the detection process. Each scan of the IMS spectrum starts when the gating grid 8 opens, and ends just before the moment the gating grid opens again some time later, as shown by pulses 52. This interval between gating grid pulses, the scan interval 53, is operator adjustable. During each of these scans, the amplified signal from the drift tube collector electrode is digitized at a constant rate, and the resulting values are stored in a buffer in a RAM 54 of the microprocessor 14. Two of these buffers are used, with the data from each consecutive scan stored alternately between the two buffers; while data is being stored in one buffer, the data from the previous scan in the other buffer is processed.

The data for several scans are added together before further processing to improve the signal to noise ratio and hence the sensitivity of the detector. To carry this out, the processor uses a second pair of summing buffers 55. Once a scan is complete, the processor takes the data for each time period from the beginning of the scan and adds it to the appropriate value in a summing buffer. This is carried out for a user-selectable number of scans which constitutes a complete data collection cycle for one sample. As shown in FIG. 3, for a scan interval (δT) of 20 ms and an integration value (number of sweeps or scans) of 16, a complete sample analysis cycle takes 320 ms.

After a complete data cycle, the processor 14 has a sum buffer filled with summed data from all the scans of that cycle. It now starts summing the subsequent scans from the next data collection cycle into the other summing buffer 55 and simultaneously starts processing the filled summed data buffer. The signal processing 56 in the microprocessor 14, consists of basically two steps carried out for the calibrant and each of the various target channels that are being monitored. In the first step, the data is treated by algorithms 57 of a finite positive fit function that indicate the presence of correctly shaped peaks near the expected positions. The expected positions are determined from electronic look-up tables, which give expected positions relative to calibrant peak positions. If a possible peak is found, the algorithm returns and inspects the raw spectral data to confirm and define the position of that peak.

Figure 6:
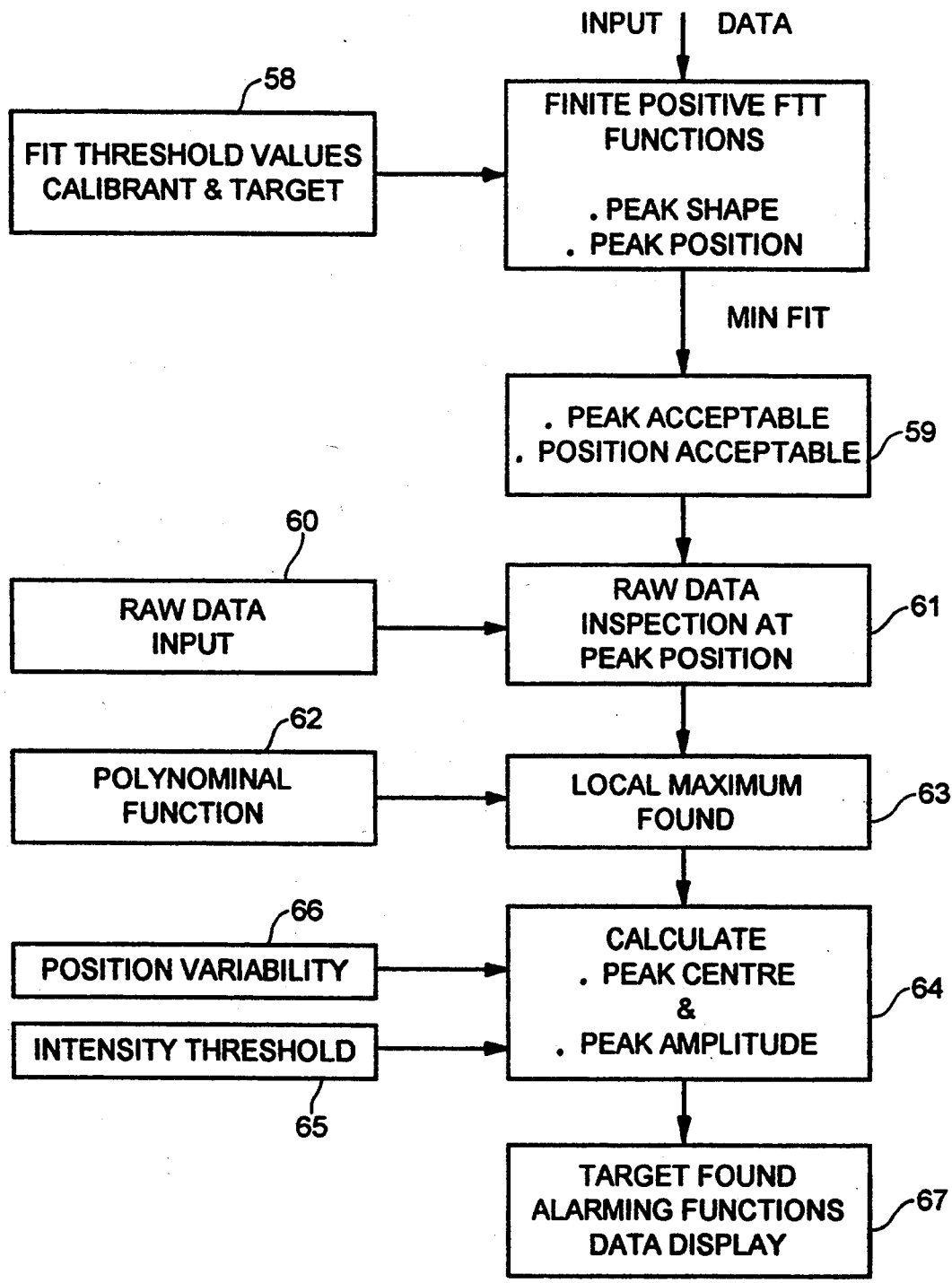
FIG. 6 is a schematic, block diagram, depicting the application of detector algorithms.

FIG. 6 shows the detailed application of a detection algorithm to the data of FIG. 5. The better the fit between the data and the expected peak shape and, to some extent, the larger the amplitude of the peak and the larger the background amplitude, the large the value of the shape/position function. Fit threshold values 58 in calibrant and channel control menus, see Table 1, are set to minimum acceptable values by means of which the algorithm decides if the peak is acceptable. The positive fit function has a finite positive value as high as 3.0, even with a flat background; hence there is a minimum acceptable threshold value below which the algorithm will produce meaningless results since it will detect peaks in a flat background. If the threshold is set too high, the algorithm will not identify any peak, no matter how good the fit. A value of 7 to 10 gives a strong spectral peak free of interferences and with the FWHM (full width at half maximum) value within 10% of the actual peak width.

If a possible peak is found from the above positive fit function, it is checked at 59 to see if it is acceptable as to peak shape and position. If so, the algorithm returns to the raw spectral data 60, and inspects the data at the indicated position for the presence of a local maximum 61. If one is identified close enough to the position indicated by the above function, then a polynomial fit 62 is carried out to calculate the local maximum 63 and the position of the center of the peak and its amplitude 64. If the amplitude is above a minimum, i.e. above a preset intensity threshold 65, and the peak is close enough to the expected position 66, which presets the allowed variability, then the peak is marked as "found" for subsequent processing—be it averaging for the calibrant, or activating an alarm 67 for the target compounds.

As noted, the time available to the detector to complete the data processing before the next data cycle starts is typically 320 ms. The amount of processing, and therefore the time required for processing, increases with the number of target channels activated, the width of the window or variability associated with each channel including the calibrant (since a wider window requires more time to search), and the FWHM (since a wider peak requires a wider window). A lower threshold value also increases data processing time since this generally means that more possible peaks need to be investigated. If data processing requires longer than the available time, data will be missed in the subsequent cycle, leading to less accurate or less timely results. Choosing instrument and analysis parameters that ensure fast processing will not only obviate these risks, but will also enable more target ion peaks to be covered in each scan. Additional channels could include the detection of a greater number of analytes thus increasing the scope of the analysis, or the detection of multiple peaks for the same analyte thus enhancing result validation. The major potential for faster processing is by reducing peak variability, for which greater ion stability, achieved through control of drift gas water content, is required.

It will now be seen that all instrumental measures should be taken to minimize variability in IMS peak positions, for both calibrant and analytes, so that the measurement window for each peak is as narrow as possible. Some variability in peak position is inevitable because ionization chemistry processes within the reactant region of the IMS produce effects that are not entirely controllable. However, one significant and controllable contributor to variability in peak drift times is the water vapor content of the drift air. With a single stage drying process, the drying material will soon deteriorate, causing the water content in the drift gas to gradually increase and peak positions to change with time. A low and essentially constant water content over an extended period of time is achieved by means of a two-stage drying process involving TE predrying by condensation at 2° to 6° C., followed by further reduction of water content to a low controlled level with a large capacity drying tube containing calcium sulphate or equivalent material, thereby achieving a significant improvement in peak stability, which allows the search algorithms to be set to narrower widths than would be otherwise achievable.

We claim:

1. A method of detecting the presence of an analyte in an ion mobility spectrometer apparatus having a drift region, a first inlet for drift gas at one end of the drift region, an outlet for exhaust gas connected to the drift region, a second inlet for a sample, and means for applying an electric field across the drift region including a collector electrode, the method comprising:
   (a) drying a supply gas to remove a major portion of the water vapor in a first drying device capable of generally continuous operation;
   (b) subjecting the supply gas to secondary drying in a second drying device capable of only a finite period of operation, to reduce water vapor content to a concentration sufficient to prevent any substantial effect on at least one predetermined analyte peak position wherein removal of the portion of the water vapor in step (a) extends an effective operating period of the second drying device and wherein the water content is reduced to a lower level than in step (a)
   (c) passing the supply gas through the drift region, as a drift gas;
   (d) introducing a sample vapor containing at least one analyte through the second inlet into the drift region; and
   (e) detecting the presence of each analyte in the sample from the drift time through the drift region.

2. The method as claimed in claim 1, wherein the IMS device includes an ionization region, a gating grid separating the ionization region from the drift region with the second inlet opening into the ionization region and the outlet being connected to the ionization region, wherein the method comprises supplying a portion of the dried supply gas to the second inlet, as a carrier gas for entraining the analyte vapor, the drift gas comprising another portion of the supply gas.

3. A method as claimed in claim 1, wherein step (a) comprises subjecting the supply gas to a temperature to cause condensation of the water vapor, and step (b) comprises passing the supply gas through a material capable of absorbing the water vapor.

4. A method as claimed in claim 3, wherein step (a) is effected using a thermo-electric cooler device, and step (b) is effected using one of calcium sulphate, phosphorus pentoxide, and a molecular sieve, as the water-absorbing material.

5. A method as claimed in claim 4, which includes the additional step of heating the material used in step (b), to reactivate the material.

6. A method as claimed in claim 3, 4 or 5, wherein in step (a) the supply gas is chilled to approximately 2° to 6° C., and in step (b), the supply gas is dried to a water content of about 1–10 μg/L.

7. A method of detecting the presence of an analyte in an ion mobility spectrometer apparatus having a drift region, an ionization region, a gating grid separating the ionization region from the drift region, a first inlet for drift gas at one end of the drift region, an outlet for exhaust gas connected to the drift region, and a second inlet for carrier gas opening into the ionization region, the method comprising:
   (a) drying a supply gas to remove a portion of water vapor in a first drying device, which chills the supply gas to a low temperature to remove water vapor by condensation and which is capable of generally continuous operation;
   (b) subjecting the supply gas to secondary drying in a second drying device capable of a finite period of operation, to reduce water vapor content to a concentration sufficient to prevent any substantial effect on at, least one predetermined analyte peak position, wherein removal of the portion of the water vapor in step (a) extends an effective operating period of the second drying device and wherein the water content is reduced to a lower level than in step (a);
   (c) passing one portion of the supply gas to the inlet of the drift region, as a drift gas, and passing another portion of the supply gas to the second inlet, as a carrier gas for analyte vapor;
   (d) introducing carrier gas containing the vapor of at least one analyte through the second inlet into the ionization region; and
   (e) detecting the presence of each analyte in the sample from the drift time through the drift region.

8. A method as claimed in claim 7 wherein step (b) comprises passing the supply gas through a material capable of absorbing water vapor, as the second drying device, to reduce the amount of water vapor in the gas.

9. A method as claimed in claim 2, 8 or 3, wherein in step (c), prior to passing the drift gas into the drift region a calibrant is added to the drift gas, and wherein the supply gas is dried to a water content of about 1–10 μg/L, and wherein step (e) comprises, for the detection of each analyte, the steps of:
   (i) providing a narrow window, and positioning that window for a desired analyte peak, by reference to a look up table of pre-set ratios of drift times of analytes to that of the calibrant;
   (ii) detecting the presence of the analyte peak in the window, by a detection algorithm.

10. A method as claimed in claim 8, wherein in step (c), prior to passing the drift gas into the drift region, a calibrant is added to the drift gas, and wherein step (e) comprises, for each analyte peak, the steps of:
   (i) providing a narrow window of substantially 80 to 120 microsecond length, and positioning that window for a desired analyte peak, by reference to a look up table of pre-set ratios of drift times of analytes to that of the calibrant;
   (ii) detecting the presence of analyte peak in the window by a detection algorithm.

11. A method as claimed in claim 10, wherein the calibrant gas has a respective calibrant peak, and wherein the analyte peak position is determined as a ratio relative to the position of the calibrant peak.

12. A method as claimed in claim 8, wherein step (a) is effected using a thermo-electric cooler device, as the first drying device, and step (b) is effected using one of calcium sulphate, phosphorus pentoxide, and a molecular sieve, as the water-absorbing material.

13. A method as claimed in claim 7, 8 or 12, wherein in step (a), the supply gas is chilled to a temperature in the range of approximately 2° to 6° C. and, following step (b), the water content of the supply gas has been reduced to about 1–10 μg/L.

14. A method as claimed in claim 7, 8 or 12, wherein the supply gas comprises air.

15. A method as claimed in claim 8 or 12, which includes the additional step of, heating the absorbent material used in step (b), to reactivate the material, when the water-absorbing capacity of the material is exhausted.

16. A method as claimed in claim 12, 4 or 5 wherein the water-absorbing material includes an indicator and, wherein the indicator is used to determine the moisture content of the material and the time for effecting one of (a) replacing the material and (b) reactivating the material.

* * * * *